US00PP33153P2

(12) United States Plant Patent
Yen et al.

(10) Patent No.: US PP33,153 P2
(45) Date of Patent: Jun. 15, 2021

(54) DRAGON FRUIT PLANT NAMED 'DF14'

(50) Latin Name: *Hylocereus undatus*
Varietal Denomination: DF14

(71) Applicants: The New Zealand Institute for Plant and Food Research Limited, Auckland (NZ); Southern Horticultural Research Institute, Tien Giang (VN)

(72) Inventors: Tran Thi Oanh Yen, Tien Giang (VN); Nguyen Nhat Truong, Tien Giang (VN); Thi Nguyen Ngoc, Tien Giang (VN); Huynh Van Chanh, Tien Giang (VN); Satish Kumar, Havelock North (NZ)

(73) Assignees: The New Zealand Institute for Plant and Food Research Limited, Auckland (NZ); Southern Horticultural Research Institute, Long Dinh (VN)

( * ) Notice: Subject to any disclaimer, the term of this patent is extended or adjusted under 35 U.S.C. 154(b) by 0 days.

(21) Appl. No.: 16/974,269

(22) Filed: Dec. 9, 2020

(51) Int. Cl.
*A01H 6/24* (2018.01)
*A01H 5/08* (2018.01)

(52) U.S. Cl.
USPC ..... Plt./156

(58) Field of Classification Search
USPC ..... Plt./156
See application file for complete search history.

*Primary Examiner* — Annette H. Para
(74) *Attorney, Agent, or Firm* — Leydig, Voit & Mayer, Ltd.

(57) ABSTRACT

A new and distinct dragon fruit plant is described. The variety resulted from selection among a population of seedlings derived from a controlled cross carried out in 2013 between RF (seed parent) (not patented) and 'LD5' (pollen parent) (not patented) located in Tien Qiang, Viet Nam. The variety was selected due to its external appearance, pink strip under the skin, eating quality and canker tolerance.

4 Drawing Sheets

Figure 1:
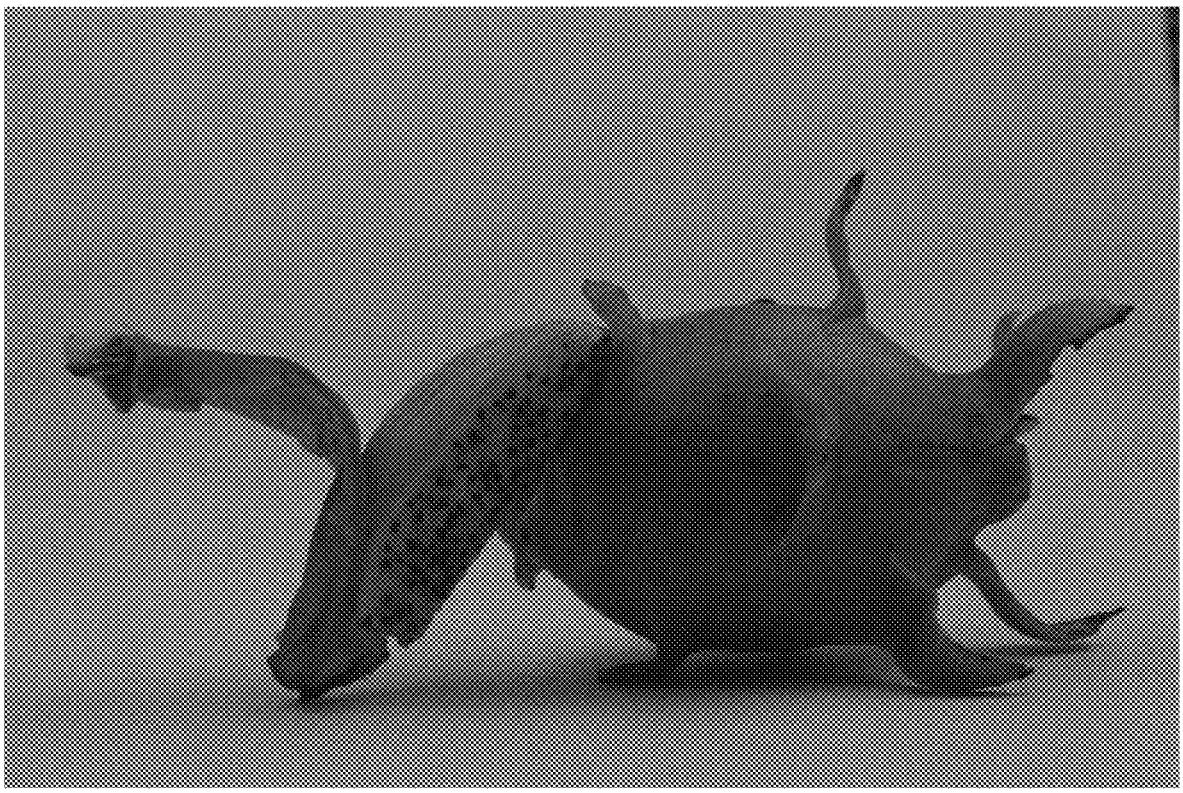

Genus and species plant named: *Hylocereus undatus.*
Variety denomination: 'DF14'.

BACKGROUND OF THE INVENTION

The plant resulted from selection among a population of seedlings derived from a controlled cross carried out in 2013 between 'RF' (seed parent) (not patented) and 'LD5' (pollen parent) (not patented) in Tien Giang, Viet Nam. 'DF14' was identified in 2016 as having potential as a new variety due to its attractive fruit appearance, good eating quality and canker tolerance. 'DF14' was first asexually propagated by cuttings in 2017, in Tien Giang, Viet Nam. The resulting plants were planted in clonal trials and underwent further evaluation. The plants were subsequently found to be true to type demonstrating that the characteristics of the new variety are stable and transmitted without change through succeeding propagations.

SUMMARY OF THE INVENTION

'DF14' is characterized by its attractive medium sized fruit with white flesh and excellent flavor; pink strip under the skin; dark pink to red skin color and tolerance to canker (*Neoscytalidium dimidiatum*).

Asexual reproduction of this new variety by cuttings and in vitro shows that the aforementioned characteristics are true to form and are established and transmitted through succeeding propagation.

COMPARISON WITH PARENTAL AND COMMERCIAL VARIETIES

TABLE 1

Comparison table between female parent and variety

| Characteristic | 'RF' | 'DF14' |
|---|---|---|
| Fruit length | Short, average 78 mm | Medium, average 98 mm |
| Fruit number of bracts | Many, average 29 | Few, average 18 |

TABLE 2

Comparison table between male parent and variety

| Characteristic | 'LD5' | 'DF14' |
|---|---|---|
| Fruit length of apical bracts | Long, average 66 mm | Medium, average 44 mm |
| Color of flesh | Near light pink, 54A | Near white, NN155D |

TABLE 3

Comparison table between commercial variety 'BT' (not patented) and variety

| Characteristic | 'BT' | 'DF14' |
|---|---|---|
| Fruit length | Long, average 122 mm | Medium, average 98 mm |
| Fruit width | Broad, average 84 mm | Medium, average 65 mm |

BRIEF DESCRIPTION OF PHOTOGRAPHS

The accompanying photographs show typical specimens of the tree, foliage and fruit of the new variety as depicted in colors as nearly true as is reasonably possible to make the same in a color illustration of this character.

FIG. 1: 'DF14' cut fruit showing pink strip under the skin.

Figure 2:
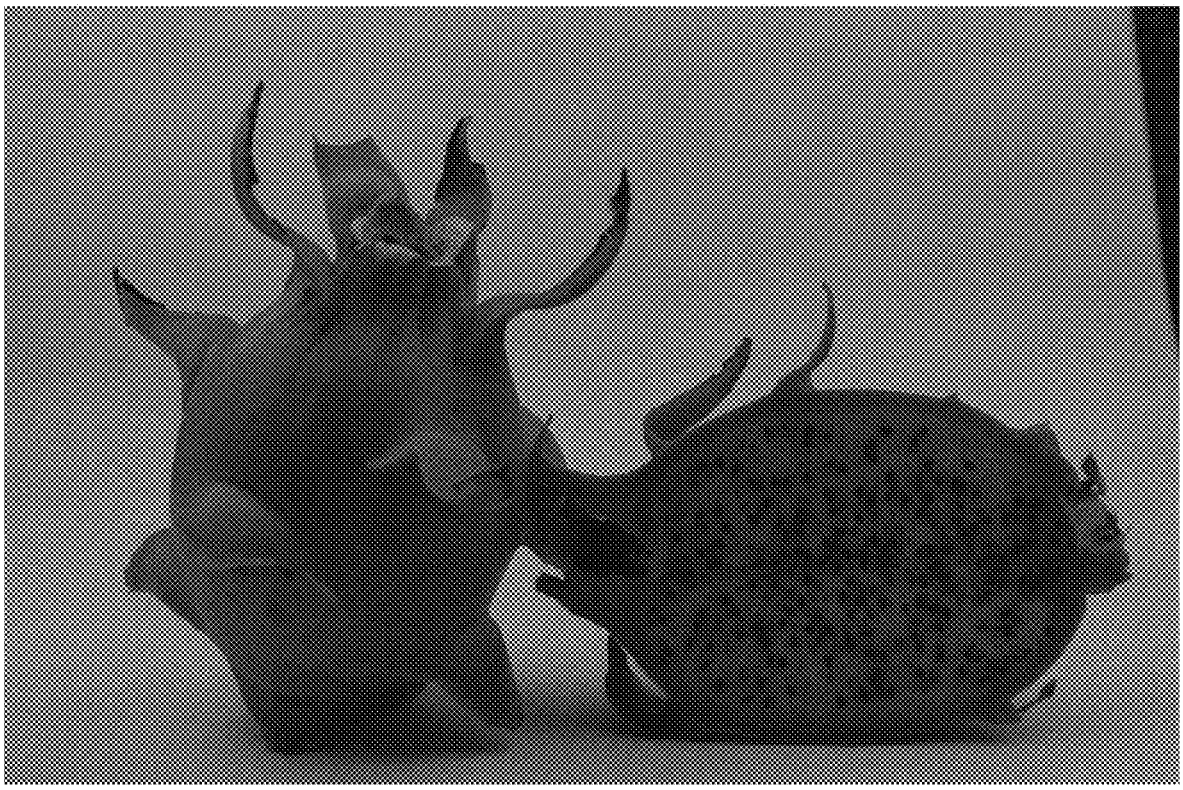

FIG. 2: 'DF14' cut fruit.

Figure 3:
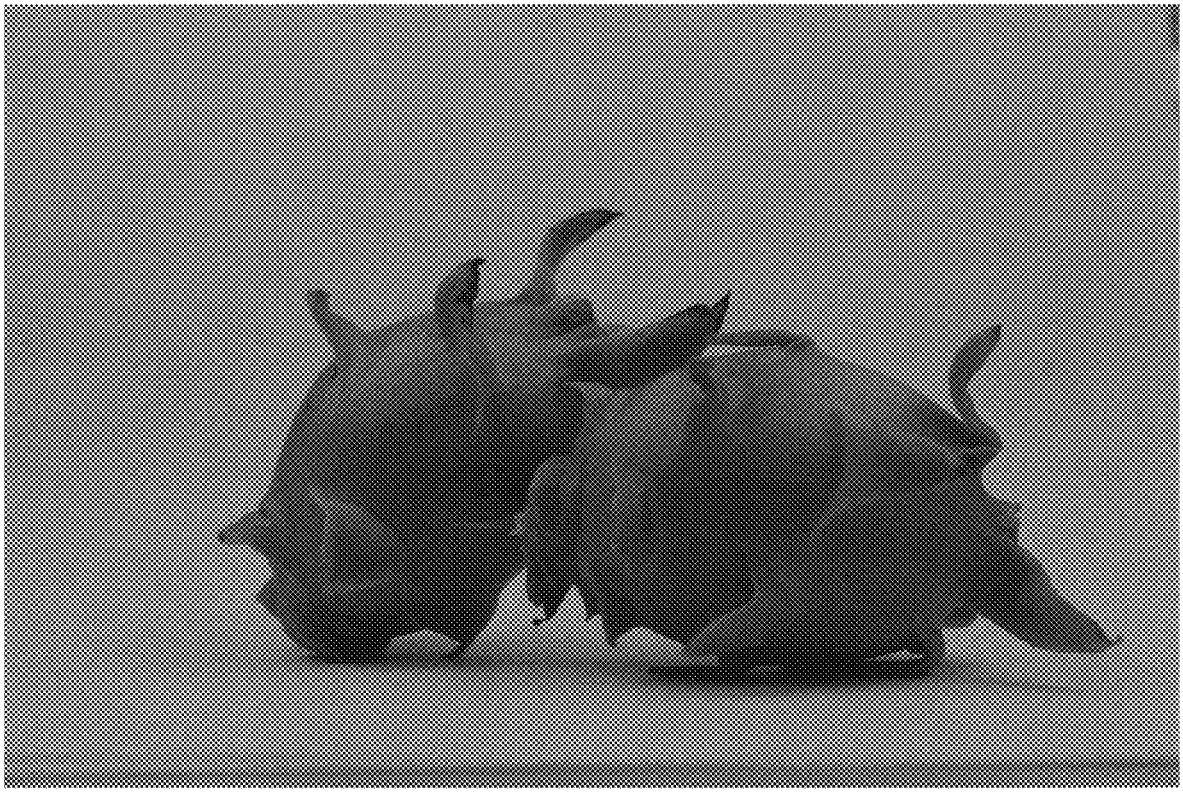

FIG. 3: 'DF14' whole fruit.

Figure 4:
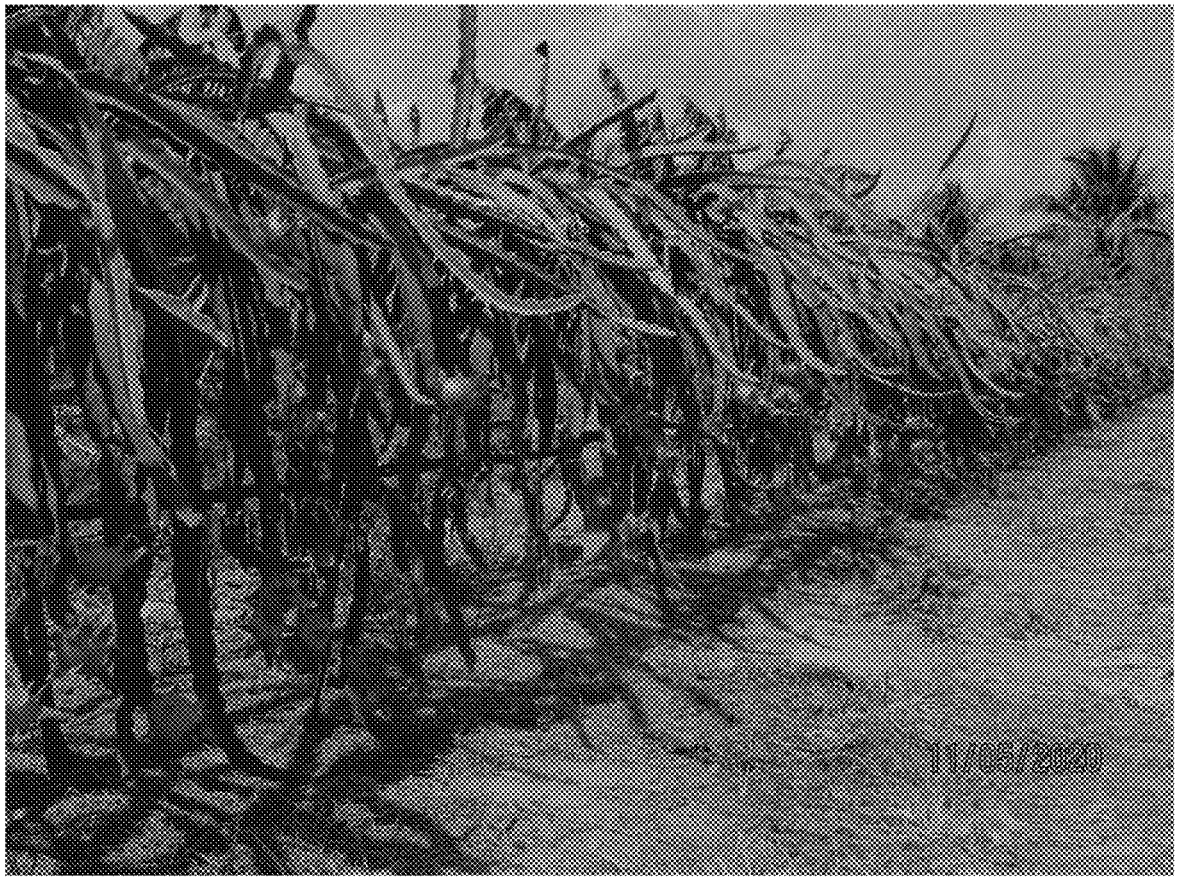

FIG. 4: 'DF14' fruit on two-year-old plant.

DETAILED DESCRIPTION

The following is a description of the new variety with color terminology in accordance with The Royal Horticultural Society Colour Charts (R.H.S.C.C.) 2015 edition.

The specimens described were grown in Tien Giang, Viet Nam. The observations were made in the 2018-2020 season on 1-2-year-old plants.

Plant:

*Form*.—Drooping.

*Vigour*.—Strong.

*Habit*.—Climbing cactus.

Young stem:

*Reddish color*.—Weak intensity.

Stem: Observation made on mature stems segment at end of year's growth.

*Shape*.—Three broad thin ribs.

*Length of segment*.—Medium, average 932 mm.

*Width*.—Medium, average 47 mm.

*Waxiness*.—Weak.

*Texture of surface*.—Smooth.

*Distance between areoles*.—Long, average 58 mm.

*Arch height*.—Medium, average 6 mm.

*Margin of rib*.—Convex.

*Intensity of grey color of areoles*.—Dark intensity.

Areoles and spins: Observations made on intact mature stems.

*Number of spines*.—Medium, average 3.

*Spine length*.—Medium, average 4 mm.

*Spine main color*.—Near dark grey 201B.

Flower bud: Observation made 17 days after flower bud burst.

*Shape*.—Ovate.

*Shape at apex*.—Acute.

*Color*.—Near light green 144B.

*Length of pericarpel*.—Medium, average 39 mm.

*Width of pericarpel*.—Medium, average 29 mm.

*Length of perianth*.—Medium, average 28 mm.

Flower: Observations made at full flower opening.

*Intensity of red color of bract*.—Weak intensity.

*Shape*.—Bell shaped.

*Petal color*.—Near white NN155D.

*Sepal main color*.—Near light green N144D.

*Sepal pattern of secondary color*.—None.

*Length of style*.—Medium, average 25 mm.

*Number of stigma lobes*.—Many, average 26.3 mm.

*Color of stigma lobe*.—Cream.

*Position of anthers in relation to stigma*.—Same level to above.

*Flowering time*.—Early April; nocturnal; 'DF14' starts flowering earlier than commercial cultivars such as 'LD1' and 'LD5'.

Fruit: Observations made on 5 intact fruit fully mature for consumption 3 to 5 days after first color change.

*Length*.—Medium, average 98 mm.

*Width*.—Medium, average, 65 mm.

*Weight*.—Medium, 255 g.

*Ratio length/width*.—Medium.

*Number of bracts*.—Few, average 18.

*Length of apical bracts*.—Medium, average 44 mm.

*Position of bracts towards the peel*.—Strongly held out, average 3 mm.

*Main color of middle bracts*.—Near light green 144A.

*Width of the base of the bracts*.—Medium, average 29 mm.

*Thickness of peel*.—Thick, average 2 mm.

*Color of peel* (*excluding bracts*).—Near light pink, 51B.

*Color of flesh*.—Near white, NN155D.

*Sweetness*.—Medium, brix 16.7.

*Apical cavity*.—Medium, average 21 mm.

*Seed size*.—Small to medium.

*Harvest*.—Mid May to the end of November.

Use: Fresh market.

*Disease*.—Tolerant to canker *Neoscytalidium dimidiatum*.

The invention claimed is:

1. A new and distinct dragon fruit plant substantially as illustrated and described herein.

* * * * *